(12) United States Patent
Yan et al.

(10) Patent No.: US 12,354,274 B2
(45) Date of Patent: Jul. 8, 2025

(54) SYSTEM AND METHOD FOR MACHINE LEARNING BASED TRACKINGLESS IMAGING VOLUME RECONSTRUCTION

(71) Applicant: Rensselaer Polytechnic Institute, Troy, NY (US)

(72) Inventors: Pingkun Yan, Clifton Park, NY (US); Hengtao Guo, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 423 days.

(21) Appl. No.: 17/558,869

(22) Filed: Dec. 22, 2021

(65) Prior Publication Data

US 2022/0270259 A1    Aug. 25, 2022

Related U.S. Application Data

(60) Provisional application No. 63/151,984, filed on Feb. 22, 2021.

(51) Int. Cl.
*G06T 7/00* (2017.01)
*A61B 8/00* (2006.01)
(Continued)

(52) U.S. Cl.
CPC .............. *G06T 7/0016* (2013.01); *A61B 8/44* (2013.01); *G06V 10/36* (2022.01); *G06V 10/454* (2022.01);
(Continued)

(58) Field of Classification Search
CPC . G06T 2207/10132; G06T 2207/10136; G06T 7/30; G06T 7/32; G06T 7/33;
(Continued)

(56) References Cited

U.S. PATENT DOCUMENTS 8,116,549 B2    2/2012  Warmath et al.
10,074,038 B2   9/2018  Hsieh et al.
(Continued)

FOREIGN PATENT DOCUMENTS

JP    6713563 B2   6/2020
WO    1998024065   6/1998
(Continued)

OTHER PUBLICATIONS

Prevost, Raphael, et al. "3D freehand ultrasound without external tracking using deep learning." Medical image analysis 48 (2018): 187-202. (Year: 2018).*

(Continued)

*Primary Examiner* — Raphael Schwartz
(74) *Attorney, Agent, or Firm* — Barclay Damon LLP; Anthony P. Gangemi

(57) ABSTRACT

A method of ultrasound image volume reconstruction includes: providing a convolutional neural network ("CNN"); receiving a first dataset comprising at least one pair of consecutive ultrasound images; inputting the first dataset to the CNN; training the CNN with the first dataset; receiving a second dataset comprising an ultrasound video comprising a plurality of consecutive ultrasound images; inputting the second dataset to the CNN; and processing, by the CNN, the second dataset to produce as output a reconstructed 3D ultrasound image volume.

17 Claims, 17 Drawing Sheets

(51) Int. Cl.
*G06V 10/36* (2022.01)
*G06V 10/44* (2022.01)
*G06V 10/82* (2022.01)

(52) U.S. Cl.
CPC .... *G06V 10/82* (2022.01); *G06T 2207/10136* (2013.01)

(58) Field of Classification Search
CPC .... G06T 7/35; G06T 7/37; G06T 7/38; A61B 8/4263; A61B 8/4254; A61B 8/4245; A61B 8/483
See application file for complete search history.

(56) References Cited

U.S. PATENT DOCUMENTS

| | | | |
|---|---|---|---|
| 10,127,659 | B2 | 11/2018 | Hsieh et al. |
| 10,134,155 | B2 | 11/2018 | Lachaine |
| 10,242,450 | B2 | 3/2019 | Prevost et al. |
| 10,282,588 | B2 | 5/2019 | Comaniciu et al. |
| 2018/0018757 | A1 | 1/2018 | Suzuki |
| 2018/0177461 | A1 | 6/2018 | Bell et al. |
| 2019/0147589 | A1 | 5/2019 | Zhou et al. |
| 2019/0172219 | A1 | 6/2019 | Bharara |
| 2019/0180143 | A1 | 6/2019 | Lyu |
| 2019/0244389 | A1 | 8/2019 | Kusakabe |
| 2019/0254624 | A1* | 8/2019 | Wood ................ A61B 8/12 |
| 2019/0295295 | A1 | 9/2019 | Hyun et al. |
| 2019/0318476 | A1 | 10/2019 | Isgum et al. |
| 2019/0325620 | A1 | 10/2019 | Adler et al. |
| 2019/0340470 | A1 | 11/2019 | Hsieh et al. |
| 2019/0378311 | A1 | 12/2019 | Mailhe et al. |

FOREIGN PATENT DOCUMENTS

| | | |
|---|---|---|
| WO | 2018023001 A1 | 2/2018 |
| WO | 2019109613 A1 | 6/2019 |
| WO | 2019166332 A1 | 9/2019 |
| WO | 2020018819 A1 | 1/2020 |
| WO | 2021146497 A1 | 7/2021 |

OTHER PUBLICATIONS

Jaderberg, Max, Karen Simonyan, and Andrew Zisserman. "Spatial transformer networks." Advances in neural information processing systems 28 (2015). (Year: 2015).*

* cited by examiner

| Method | Target Supervision | Source Domain (Transrectal Scans) | | | | | | | Target Domain (Abdominal Scans) | | | | | | |
|---|---|---|---|---|---|---|---|---|---|---|---|---|---|---|---|
| | | Distance Error (mm) | | | | Final Drift (mm) | | | Distance Error (mm) | | | | Final Drift (mm) | | |
| | | Min | Median | Max | Avg | Min | Median | Max | Avg | Min | Median | Max | Avg | Min | Median | Max | Avg |
| Source | No | 2.64 | 9.33 | 27.33 | 11.11 | 4.01 | 15.14 | 65.78 | 19.71 | 7.31 | 14.35 | 21.59 | 15.73 | 11.87 | 28.15 | 43.66 | 25.73 |
| ADDA | | - | - | - | - | - | - | - | - | 7.28 | 13.64 | 20.01 | 14.88 | 9.45 | 23.76 | 38.83 | 22.48 |
| Mixed | Fully | 6.14 | 16.67 | 34.28 | 16.64 | 5.28 | 28.57 | 78.81 | 30.52 | 8.27 | 12.65 | 19.16 | 13.36 | 8.03 | 21.42 | 35.97 | 21.33 |
| Target | | 7.15 | 15.69 | 37.07 | 16.71 | 4.46 | 26.93 | 79.11 | 29.71 | 7.42 | 11.49 | 18.65 | 12.52 | 5.88 | 21.21 | 32.94 | 20.01 |
| TAUVR | Weakly | - | - | - | - | - | - | - | - | 7.31 | 10.02 | 20.68 | 12.67 | 6.87 | 22.02 | 32.13 | 20.34 |

FIG. 14

SYSTEM AND METHOD FOR MACHINE LEARNING BASED TRACKINGLESS IMAGING VOLUME RECONSTRUCTION

CROSS REFERENCE TO RELATED APPLICATION(S)

This application claims the benefit of U.S. Provisional Patent Application No. 63/151,984, filed Feb. 22, 2021, which is incorporated by reference as if disclosed herein in its entirety.

STATEMENT REGARDING FEDERALLY SPONSORED RESEARCH AND DEVELOPMENT

The present invention was made with government support under Grant No. EB028001 and Grant No. EB027898 awarded by the United States National Institutes of Health. The government has certain rights in the invention.

FIELD

The present technology generally relates to the area of imaging volume reconstruction. More particularly, the present technology relates to imaging volume reconstruction of sensorless ultrasound scans.

BACKGROUND

Ultrasound imaging has been widely used in interventional applications to monitor and trace target tissue. Ultrasound possesses many advantages, such as low cost, portable setup, and the capability of navigating through patients in real-time for anatomical and functional information. Transrectal ultrasound imaging ("TRUS") has been commonly used for guiding prostate cancer diagnosis and can significantly reduce the false negative rate when fused with magnetic resonance imaging ("MRI"). However, two-dimensional ("2D") ultrasound images are difficult to be registered with three-dimensional ("3D") MRI volume, due to the differences in not only image dimension but also image appearance. In practice, a reconstructed 3D ultrasound image volume is usually required to assist such interventional tasks.

A reconstructed 3D ultrasound imaging volume visualizes a 3D region of interest ("ROI") by using a set of 2D ultrasound frames, which can be captured by a variety of scanning techniques such as mechanical scan and freehand tracked scan. Among these categories, the tracked freehand scanning is the most favorable method in many clinical scenarios. For instance, during a prostate biopsy, the freehand scanning allows clinicians to freely move the ultrasound probe around the ROI and produces ultrasound images with much more flexibility. The tracking device, either an optical or electro-magnetic ("EM") tracking system, helps to build a spatial transformation chain between the imaging planes in the world coordinate for 3D reconstruction.

Ultrasound volume reconstruction from sensorless freehand scans takes this a step further by removing the tracking devices attached to the ultrasound probe. The prior research on this was mainly supported by the speckle decorrelation, which maps the relative difference of position and orientation between neighboring ultrasound images to the correlation of their speckle patterns, i.e. the higher the speckle correlation, the lower the elevational distance between neighboring frames. By removing the tracking devices, such sensorless reconstruction allows the clinicians to move the probe with less constraint without being concerned about blocking tracking signals. It also reduces the hardware cost. Although the speckle correlation carries information of the relative transformation between neighboring frames, relying on the decorrelation alone renders unreliable performance.

In recent years, deep learning ("DL") methods based on convolutional neutral networks ("CNN") have been identified as an important tool for automatic feature extraction. In the field of ultrasound volume reconstruction, the feasibility of using CNN to directly estimate the inter-frame motion between 2D ultrasound scans has been explored. A network with 2D convolutional layers estimates the relative rotations and translations between two consecutive frames. However, a typical ultrasound scanning video contains rich contextual information beyond two neighboring frames. Using only two neighboring frames loses temporal information and results in less accurate reconstruction.

Thus, a need exists for an improved machine learning system for sensorless freehand 3D ultrasound image volume reconstruction that addresses the problems described above.

SUMMARY

According to an embodiment of the present technology, a method of ultrasound image volume reconstruction is provided. The method includes: providing a convolutional neural network ("CNN"); receiving a first dataset comprising at least one pair of consecutive ultrasound images; inputting the first dataset to the CNN; training the CNN with the first dataset; receiving a second dataset comprising an ultrasound video comprising a plurality of consecutive ultrasound images; inputting the second dataset to the CNN; and processing, by the CNN, the second dataset to produce as output a reconstructed 3D ultrasound image volume.

In some embodiments, the CNN includes a spatial transformation network ("STN") and a loss function.

In some embodiments, the STN includes a localization network, a grid generator, and an image sampler.

In some embodiments, the localization network is configured to produce a plurality of transformation parameters for determining a position of a second image of the at least one pair of consecutive ultrasound images relative to a first image of the at least one pair of consecutive ultrasound images.

In some embodiments, the grid generator is configured to receive the plurality of transformation parameters as input and generate a plurality of 3D grids as output.

In some embodiments, the image sampler is configured to produce a reconstructed 3D ultrasound image volume by locating corresponding pixel values in the first image and the second image and filling in the plurality of 3D grids with the corresponding pixel values.

In some embodiments, the loss function includes a mean squared error loss between the outputs of a localization network of the STN and a ground-truth six degrees of freedom of the first dataset, and an image similarity loss between a reconstructed 3D ultrasound image volume of the STN and the ground-truth.

In some embodiments, the CNN includes a Deep Contextual Learning Network ("DCL-Net") and a loss function.

In some embodiments, the DCL-Net includes a Conv-Block, a plurality of 3D residual blocks, and a self-attention block.

In some embodiments, the ConvBlock is configured to convert an EM tracked vector of a first image of the plurality of consecutive ultrasound images to a 3D homogeneous transformation matrix.

In some embodiments, the plurality of 3D residual blocks are configured to extract mapping features between the plurality of consecutive ultrasound images along a temporal axis.

In some embodiments, the self-attention block is configured to receive as input a features map produced by the plurality of 3D residual blocks and generate as output an attention map to call attention to predetermined regions of the features map.

In some embodiments, the loss function includes a mean squared error loss between the outputs of the DCL-Net and a ground-truth six degrees of freedom of the first dataset, and a case-wise correlation loss between an estimated motion pattern of the ultrasound scan used to obtain the first dataset and a ground-truth mean of the first dataset. The total loss is the summation of the mean squared error loss and the case-wise correlation loss.

In some embodiments, the ultrasound video of the second dataset is obtained from a trackingless ultrasound scan such that the second dataset does not include positional information.

In some embodiments, the first dataset is obtained by a first ultrasound transducer and the second dataset is obtained by a second ultrasound transducer. The first ultrasound transducer and the second ultrasound transducer are configured to perform different ultrasound scans.

In some embodiments, the first ultrasound transducer is configured to perform transrectal ultrasound scans and the second ultrasound transducer is configured to perform transabdominal ultrasound scans.

In some embodiments, processing the second dataset includes: aligning a first image of the ultrasound images of the first dataset and a first image of the ultrasound images of the second dataset; computing a degree of freedom motion vector for each ultrasound image of the first dataset and the second dataset; forming a subsequence pool for the first dataset based on the degree of freedom motion vectors for the ultrasound images of the first dataset; searching, for each degree of freedom motion vector of the ultrasound images of the second dataset, the subsequence pool for a degree of freedom motion vector of the ultrasound images of the first dataset that most closely matches the motion vector of the ultrasound image of the second dataset; and forming a paired subsequence for each matching motion vectors of the first dataset and the second dataset.

Further objects, aspects, features, and embodiments of the present technology will be apparent from the drawing figures and below description.

BRIEF DESCRIPTION OF DRAWINGS

FIG. 14 is a chart comparing the performance of different imaging volume reconstruction methods on two different ultrasound scan videos.

DETAILED DESCRIPTION

Accordingly, embodiments of the present technology are directed to systems and methods of sensorless freehand ultrasound 3D ultrasound image volume reconstruction. Some embodiments use a Deep Contextual Learning Network ("DCL-Net"). In some embodiments, the underlying framework takes multiple consecutive ultrasound frames as input, instead of only two neighboring frames, to estimate the trajectory of the ultrasound probe by efficiently exploiting the rich contextual information. In some embodiments, to make the network focus on the speckle-rich image areas to utilize the decorrelation between frames, the attention mechanism is embedded in the network architecture. Some embodiments include a case-wise correlation loss to enhance the discriminative feature learning to prevent overfitting the scanning style.

Figure 1:
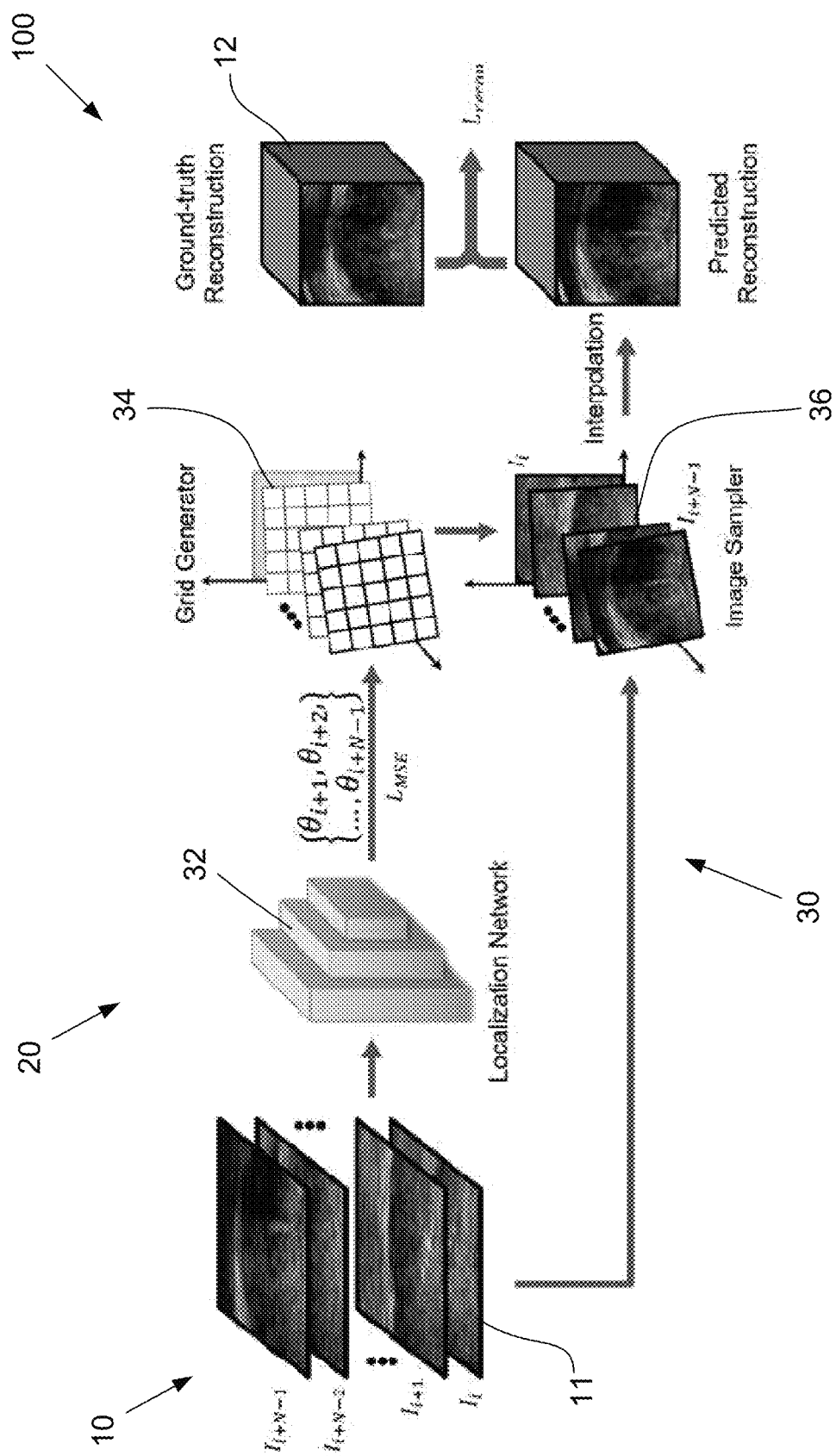
FIG. 1 is a flowchart showing an imaging volume reconstruction method according to an exemplary embodiment of the present technology.

In some embodiments, the reconstruction system of the present technology performs end-to-end deep learning/training for 3D volume reconstruction from 2D frames. FIG. 1 shows an overview of the reconstruction system 100 according to an exemplary embodiment of the present technology. The system 100 takes a number N of ultrasound 2D frames 10 as input. A sequence of a plurality of 2D ultrasound frames provides a more general representation of the motion trajectory of the ultrasound probe. A convolutional neural network ("CNN") 20 is used to extract image features from the input frames 10. The output is a reconstructed ultrasound volume. The system 100 requires a learning process. In some embodiments, at the training data acquisition process, an electro-magnetic ("EM") tracking device is used to track the ultrasound probe motion (not shown), which provides the ground-truth data for use as the ground-truth reconstruction 12. Since the ground-truth transformation matrix for each frame 10 is already available in the dataset, the reconstruction system 100 is trained in a supervised fashion with the labeled data. Thus, the volume reconstruction system 100 in some embodiments is built in an end-to-end fashion by introducing a volume reconstruction loss.

In some exemplary embodiments discussed herein, transrectal ultrasound imaging ("TRUS") scanning videos were collected by an EM-tracking device from real clinical cases. The dataset contains 640 TRUS videos all from different subjects acquired by a Philips iU22 scanner in varied lengths. Every frame 10 corresponds to an EM tracked vector that contains the position and orientation information of that frame 10. This vector is converted to a 3D homogeneous transformation matrix M=[R T; 0 1], wherein R is a 3×3 rotation matrix and T is a 3D translation vector. The primary task of 3D ultrasound reconstruction is to obtain the relative spatial position of two or more consecutive ultrasound frames. In an exemplary embodiment, two neighboring frames 10 (i.e. a pair 11) are used for illustration. Let $I_i$ and $I_{i+1}$ denote two consecutive ultrasound frames with corresponding transformation matrices $M_i$ and $M_{i+1}$, respectively. The relative transformation matrix $M_i'$ can be computed as $M_i'=M_{i+1}M_i^{-1}$. By decomposing M into six degrees of freedom ("DOF") $\theta_i=\{t_x,t_y,t_z,\alpha_x,\alpha_y,\alpha_z\}$, which contains the translations in millimeters and rotations in degrees, this $\theta_i$ computed from EM tracking is used as the ground-truth for training the system 100.

In some embodiments, for a training batch of frames 10, the system 100 iteratively passes one or more, and preferably all, neighboring pairs 11 of ultrasound image frames 10 to the CNN 20 and gets the relative position prediction for each pair. In some embodiments, the CNN 20 includes a spatial transformation network ("STN") 30 for performing intra-network volume reconstruction in 3D space. As shown in FIG. 1, the STN 30 includes, in some embodiments, three major components: (1) a localization network 32, (2) a grid generator 34, and (3) an image sampler 36. The localization network 32 produces six transformation parameters that determines the position of a second image frame 10 of the pair 11 relative to a first image frame 10 of the pair 11. However, the present technology contemplates the localization network 32 producing a different number of transformation parameters, such as less than six, up to six, or more than six. The grid generator 34 takes the transformation parameters as input and generates grids in 3D space. Based on the 3D grids, the image sampler 36 finds the corresponding pixel values in the second image frame 10 of the pair 11 and fills them into the 3D grids. Both the grid generator 34 and the image sampler 36 are preferably implemented using convolutional operations where the gradients can be back-propagated. Such design patterns make it possible to train the entire system 100 in an end-to-end fashion.

In some embodiments, the system 100 includes a loss function having two loss terms for regularizing the training progress: (1) a mean squared error ("MSE") loss $L_{MSE}$ between the outputs of localization network 32 and the ground-truth six DOF; and (2) the image similarity loss $L_{recon}$ between the reconstructed volumes from the outputs from the image sampler 36 and the ground-truth 12. Once the training is complete, the system 100 produces a reconstructed 3D ultrasound volume for a 2D ultrasound scanning video, without requiring any positional information given by a tracking device.

Figure 2:
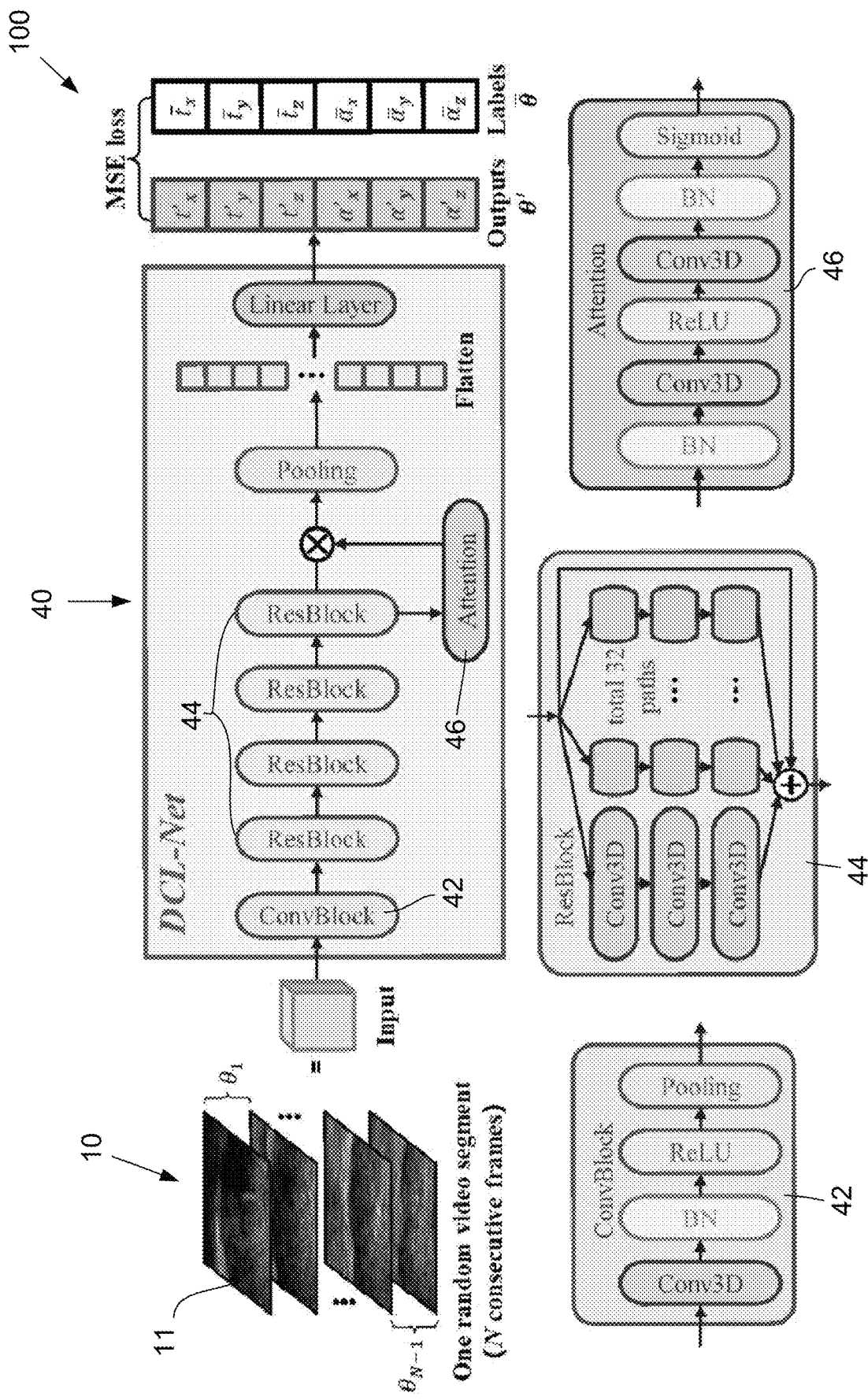
FIG. 2 is a flowchart showing an imaging volume reconstruction method according to another exemplary embodiment of the present technology.

FIG. 2 shows an overview of the reconstruction system 100 according to another exemplary embodiment of the present technology. The system 100 takes a number N of ultrasound 2D frames 10 as input. The system 100 includes a DCL-Net 40 configured to perform the image volume reconstruction. In some embodiments, the DCL-Net 40 is, or is a sub-network of, the CNN 20. In some embodiments, the DCL-Net 40 is designed on top of a 3D ResNext model. The DCL-Net 40 includes a ConvBlock 42 (e.g., a concatenation of two convolutional layers), a plurality of 3D residual blocks 44, a self-attention block 46. The ConvBlock 42 converts an EM tracked vector of a first image frame of the consecutive image frames 10 to a 3D homogenous transformation matrix. The 3D residual blocks 44 extract mapping features between the consecutive image frames 10 along a temporal axis to form a features map. The self-attention block 46 receives the features map and generates an attention map that assigns more weight to predetermined regions of the features map to call attention to the predetermined regions. In some embodiments, the predetermined regions of the features map are regions with strong speckle patterns for correlation that are of high importance in estimating the transformation. In some embodiments, the DCL-Net 40 includes basic CNN layers, such as pooling, flattening, and linear layers. The DCL-Net 40 uses skip connections help preserve the gradients to train very deep networks. The use of the multiple pathways (cardinalities) enables the extraction of important features. As shown in FIG. 2, 3D convolutional kernels are used instead of 2D convolutional kernels, mainly because 3D convolutions better extract the feature mappings along the axis of channel, which is the temporal direction here. Such properties enable the DCL-Net 40 to focus on the slight displacement of image features between consecutive frames 10 (e.g., pairs 11). Thus, the system 100 is trainable to connect the speckle correlated features to estimate the relative position and orientation change.

Figure 3:
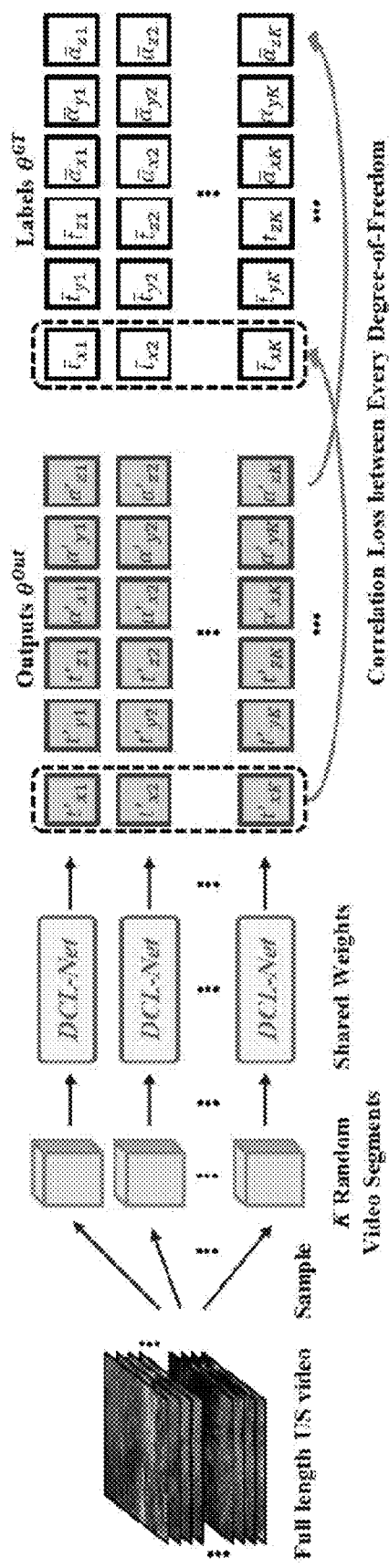
FIG. 3 is a flowchart showing the case-wise correlation loss computation of the imaging volume reconstruction method of FIG. 2.

In some embodiments, the system 100 includes a loss function having two loss terms for regularizing the training progress: (1) the MSE loss as described above regarding FIG. 1; and (2) a case-wise correlation loss based on the Pearson correlation coefficient to emphasize the specific motion pattern of a scan. FIG. 3 shows a calculation workflow of the case-wise correlation loss according to an exemplary embodiment. K video segments with each having N image frames 10 are randomly sampled from a TRUS video. The correlation coefficients between the estimated motion and the ground-truth mean are computed for every degree-of-freedom and the loss is denoted as $$L_{corr} = 1 - \frac{1}{6}\sum_{d=1}^{6} \frac{C_{ov}(\theta_d^{GT}, \theta_d^{Out})}{\sigma(\theta_d^{GT}, \theta_d^{Out})} \quad (1)$$

where $C_{ov}$ gives the covariance and $\sigma$ calculates the standard deviation. The total loss is the summation of the MSE loss and the case-wise correlation loss.

Figure 4:
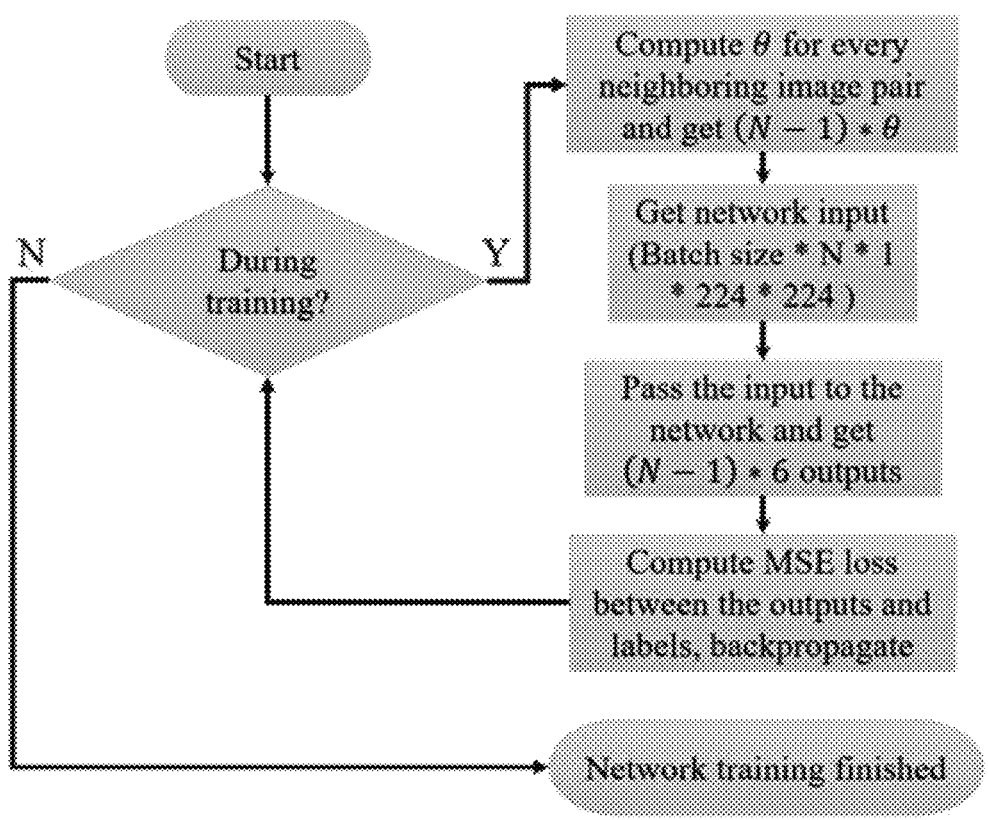
FIG. 4 is a flowchart showing the training phase of an imaging volume reconstruction method according to an exemplary embodiment of the present technology.

FIG. 4 shows a flow chart of a method of training the system 100 according to an exemplary embodiment of the present technology. During the network training, the method concatenates N consecutive ultrasound frames $I_i$, $i_{i+1}$, $I_{i+2}$, $I_{i+N-1}$ as one 3D input sample. The last fully connected layer of the network produces (N−1)*6 values to regress the target transformation parameters. In some embodiments, the learning progress is restricted by imposing a MSE loss between the network outputs and the ground-truth labels.

Figure 5:
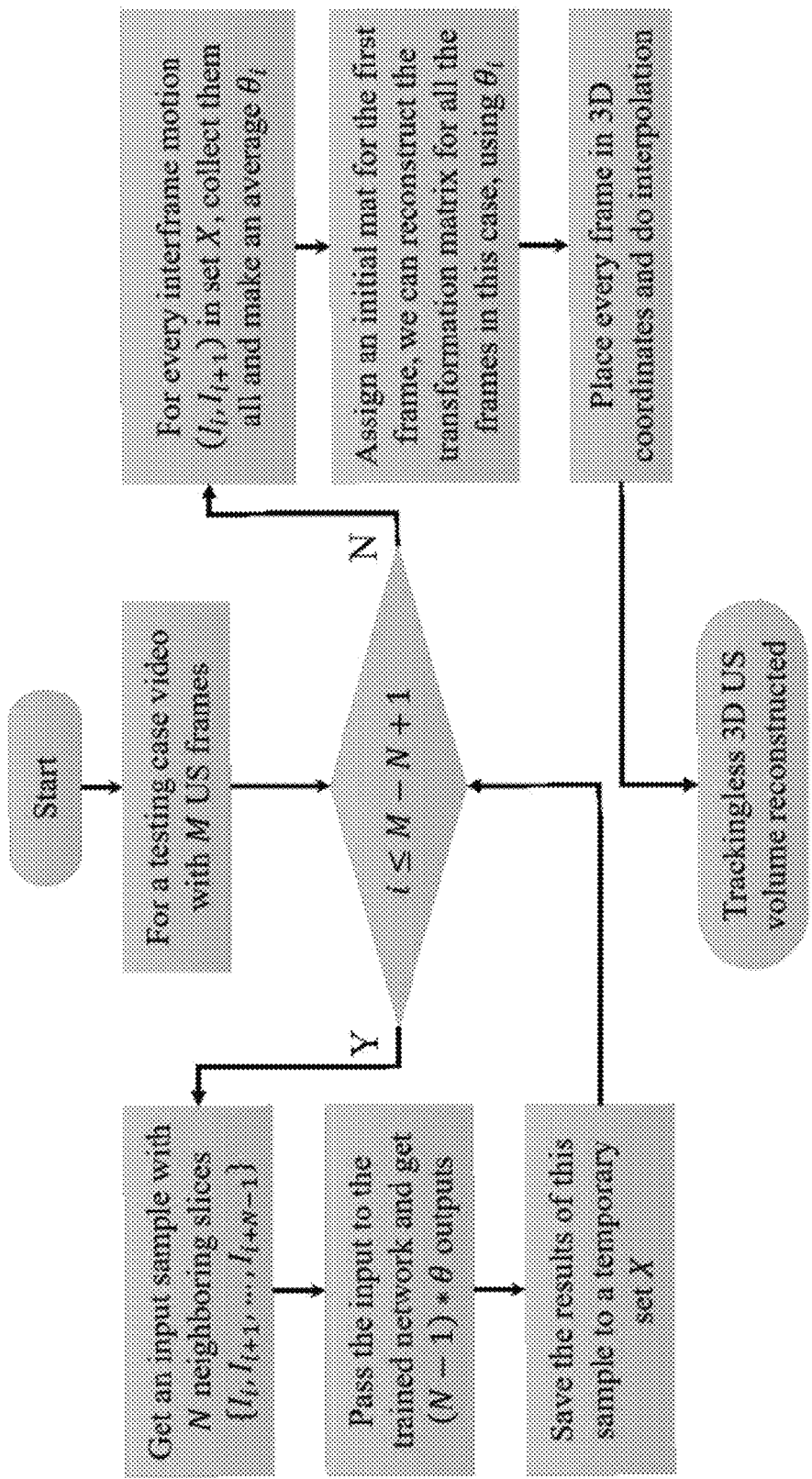
FIG. 5 is a flowchart showing the testing phase of an imaging volume reconstruction method according to an exemplary embodiment of the present technology.

FIG. 5 shows a flow chart of a method of testing the volume reconstruction performed by the system 100 according to an exemplary embodiment of the present technology. In some embodiments, once the training is complete, given M consecutive ultrasound image frames as input, the system produces the relative transformation parameters, in the form of six DOF θ, to describe the relative spatial position of two image frames of a first neighboring image frame pair. By passing through every neighboring image pairs in an ultrasound scanning video, the system outputs all interframe motions within the video. Once assigning one initial transformation matrix to the first image frame, all consecutive frames' spatial position (transformation matrix) are reconstructed using the network's outputs.

In some embodiments, during the training process, a sequence of N frames with height and width denoted by H and W, respectively, is stacked to form a 3D input volume in the shape of N×H×W. In some embodiments, $\{\theta_i | i=1, \ldots, N-1\}$ denote the relative transform parameters between the neighboring frames. Instead of directly using these parameters as ground-truth labels for network training, the mean parameters $$\bar{\theta} = \frac{1}{N-1} \sum_{i=1}^{N-1} \theta_i \qquad (2)$$

are used for the following two reasons. First, since the magnitude of motion between two frames is small, using the mean effectively smooths the noise in probe motion. Second, another advantage in practice is that there is no need to modify the output layer every time when the number of input frames is changed. An exemplary test slides along the video sequence with a window size N. The interframe motion of two neighboring image frames is the average motion computed in all the batches.

Since the method is an iterative approach, where the following transformation matrix are built upon the former ones, there is a potential risk of generating accumulative error. However, based on the observation of clinical scans, the motion of the probe was determined to be relatively smooth and continuous with negligible accelerations. Thus, the interframe motions within one video should be stable and consistent. To further eliminate the accumulative error and improve the reconstruction accuracy, some embodiments are directed to an alternative approach that directly models the ultrasound probe's motion in 3D space instead of estimating each frame's spatial position. For each DOF, a high-order-polynomial function is used to fit the trend. Then, the coefficients of all these polynomial functions are used as the ground-truth label modeling the trajectory for one video. For example, if a 5th order polynomial function is used as the model for one DOF, then the output of the network is 5*6=30-dimensional. Then, the system either uses recurrent deep learning models such as RNN and LSTM to model the frame or obtains the results from multiple batches and combines them as the final modeling of trajectory. In some embodiments, once the system has estimated the registration transformation between ultrasound frames using any of the above methods, image interpolation is applied to reconstruct the entire volume.

Figure 6A:
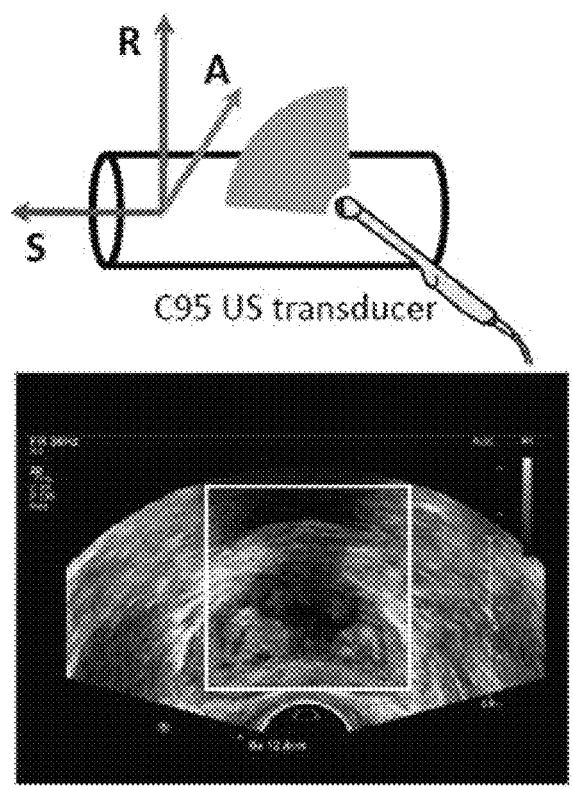
FIG. 6A shows an exemplary ultrasound transducer and transrectal ultrasound scan image.
Figure 6B:
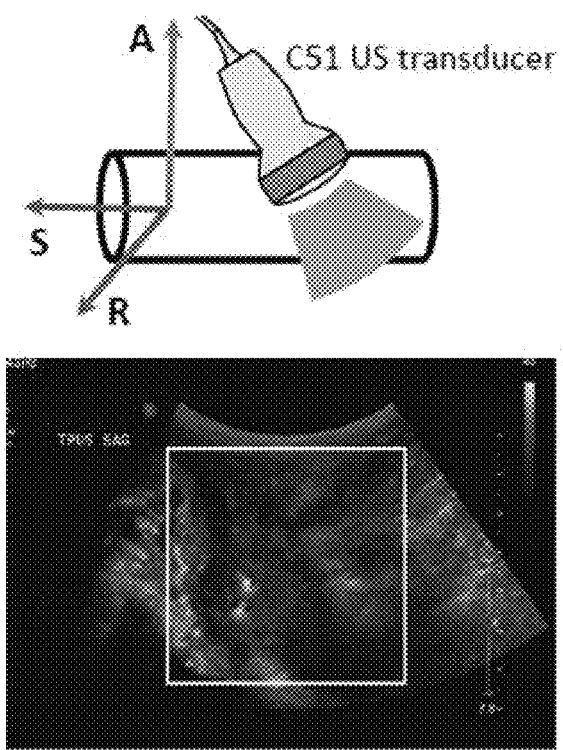
FIG. 6B shows an exemplary ultrasound transducer and transabdominal ultrasound scan image.

Embodiments of the present technology are also directed systems and methods for transducer adaptive ultrasound volume reconstruction ("TAUVR") that accounts for a potential performance degradation when performing volume reconstruction on a dataset that was obtained using a different ultrasound transducer than the ultrasound transducer that was used to obtain the training dataset. For example, as shown in FIGS. 6A-6B, both transrectal and transabdominal scans can be used to facilitate prostate cancer diagnosis, but they have distinct motion trajectories and imaging properties. Transrectal and transabdominal scans use different ultrasound transducers (e.g., the C95 ultrasound transducer shown in FIG. 6A is used for transrectal scans, and the C51 ultrasound transducer shown in FIG. 6B is used for transabdominal scans) along different motion trajectories. The cylinder in these figures represents the patient's body, and the arrows labeled R, A, and S indicate right, anterior, and superior directions, respectively. A network trained on transrectal scans may not produce satisfactory volume reconstruction on transabdominal scans. Thus, embodiments of the present technology define the transrectal scans as the source domain dataset for training the network (e.g., CNN 20 or DCL-Net 40 as discussed above). The target domain dataset denotes the new dataset where the model will be applied, such as, for example, the transabdominal scans as discussed herein. Specifically, the domain shift is caused by the difference between the two datasets, leading to the potential decrease in performance of the volume reconstruction. Embodiments of the present technology efficiently transfer the model trained on the source domain to the target domain given limited target labeled samples by reconstructing the ultrasound volume of different ultrasound transducers via domain adaptation.

In some embodiments, TAUVR is a discrepancy-based domain adaptation method having a paired-sampling strategy with feature discrepancy minimization to facilitate model adaptation from the source domain to the target domain. In some embodiments, TAUVR obtains the relative spatial position of two or more consecutive ultrasound image frames by computing a relative transformation matrix and decomposing it into six DOF, takes one video subsequence as the input for estimating the transformation parameters, and uses each subsequence's corresponding DOF vectors as the ground-truth label during the training process, as discussed above regarding system 100.

Figure 7A:
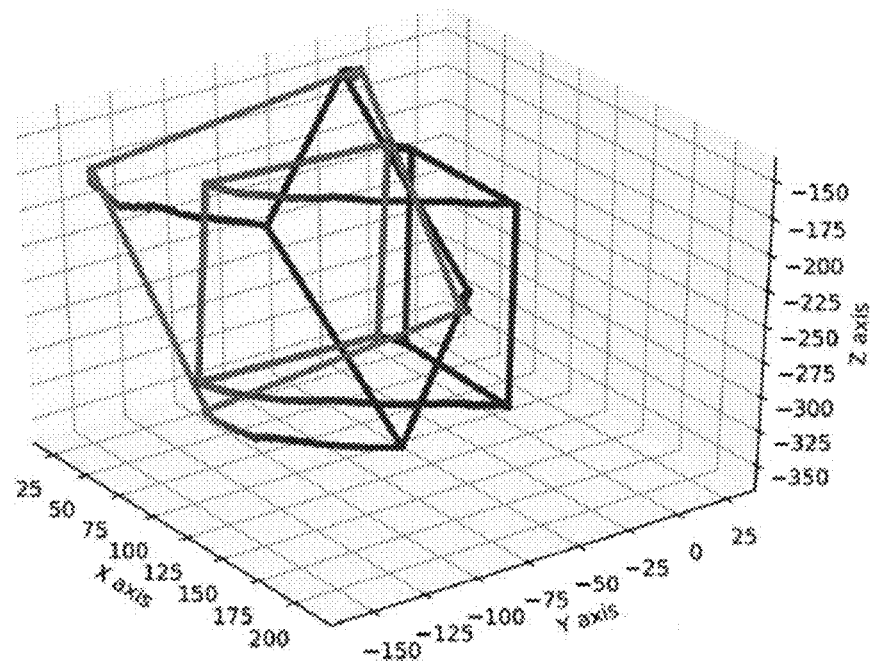
FIGS. 7A-7B show ultrasound video sequences trajectories in 3D of transrectal and transabdominal ultrasound scans before and after alignment, respectively.
Figure 7B:
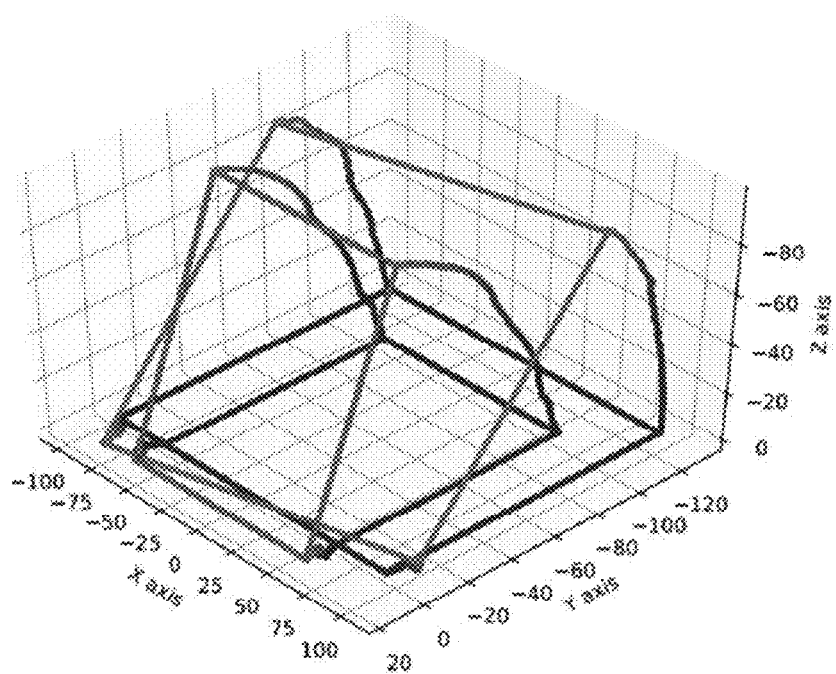
Figure 8A:
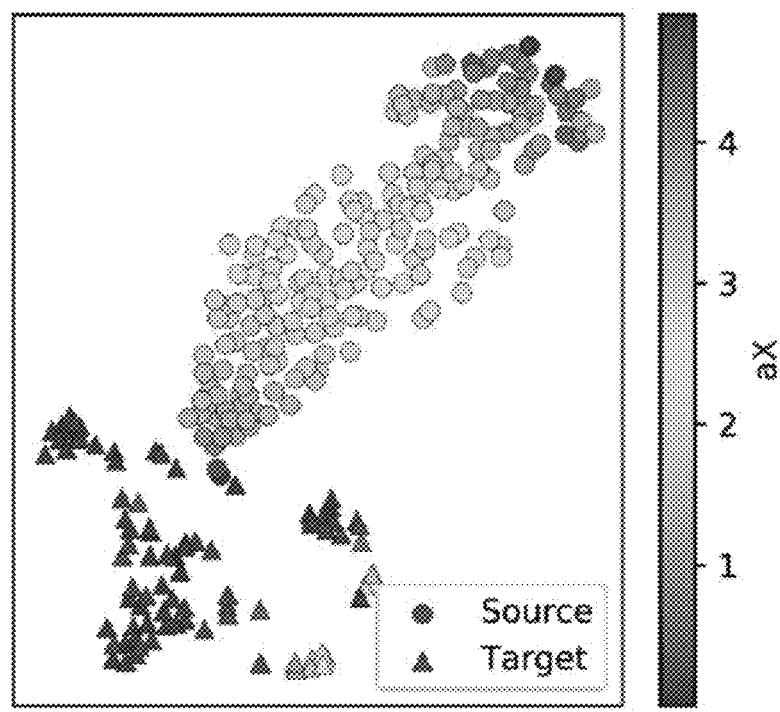
FIGS. 8A-8B show the mean degree of freedom vectors projected into 2D space for the ultrasound video sequences of FIGS. 7A-7B before and after alignment, respectively.
Figure 8B:
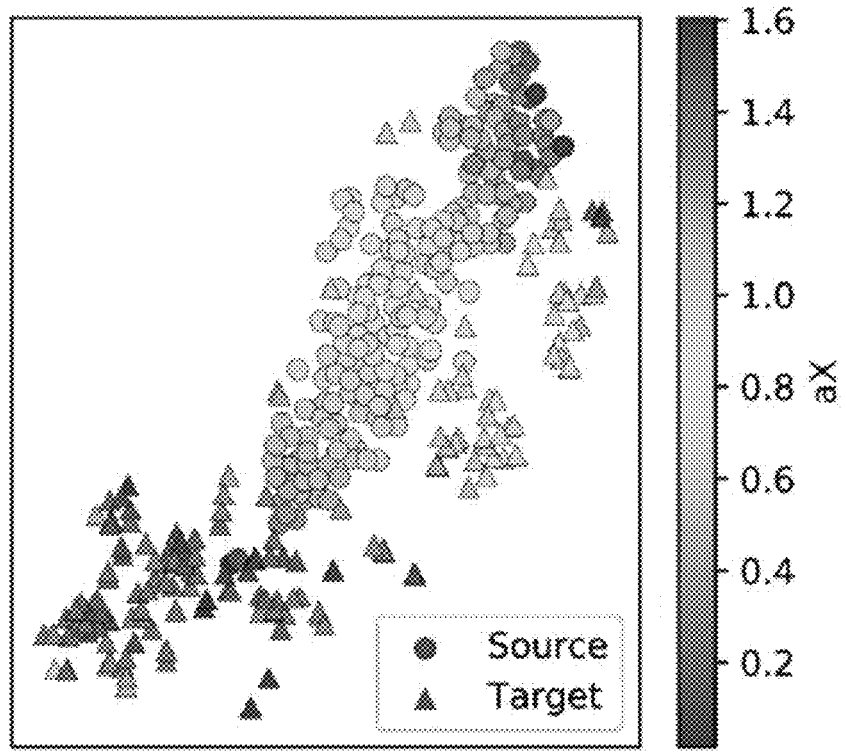

Since ultrasound transducers have different scanning trajectories for different applications, this large motion difference creates label bias that can substantially impair the network performance. Thus, some embodiments include a pre-processing step to roughly align the video sequence trajectory in 3D space, as shown in FIGS. 7A-7B. FIG. 7A shows the first image frame 10A and the last image frame 10B of a transrectal scan, and the first image frame 10C and the last image frame 10D of a transabdominal scan before alignment. FIG. 7B shows the image frames 10A, 10B, 10C, and 10D after alignment. The ultrasound videos are scaled to the same resolution and the first frames of the video sequences are aligned to the same position. The sequence rotating center (i.e. the transducer's head) is overlapping with the origin of the 3D coordinate system. Thus, the label distributions of source domain and target domain are aligned together, as shown in FIGS. 8A-8B. For each ultrasound video, a mean DOF vector is computed throughout the sequence and t-distributed stochastic neighbor embedding ("t-SNE") is used to project it into 2D space. The colorbar indicates the value of rotation aX of each case, which is the most dominant motion direction. After the alignment, the label distributions from two domains are merged into one cluster, showing a smooth aXtransition pattern. The trajectory alignment ensures that the model's performance will not be impaired by the gap label distributions. FIG. 8A shows exemplary source and target domains before trajectory alignment, and FIG. 8B shows the source and target domains after trajectory alignment.

Figure 9A:
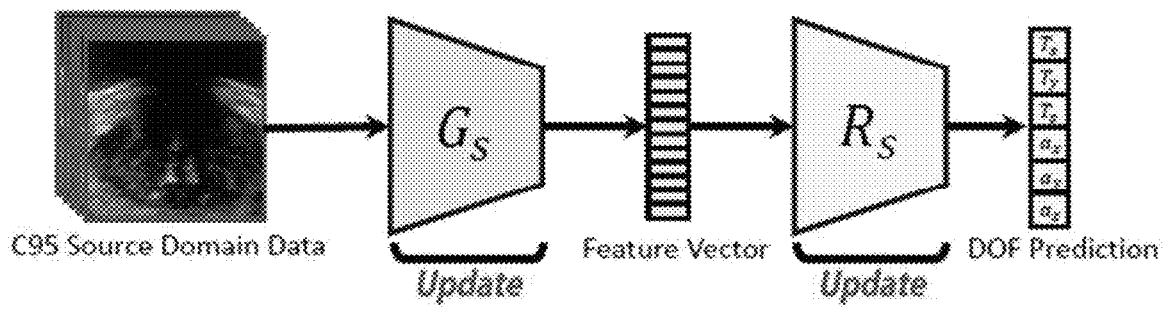
FIG. 9A is a flowchart showing the training phase of a transducer adaptive ultrasound volume reconstruction method according to an exemplary embodiment of the present technology.
Figure 9B:
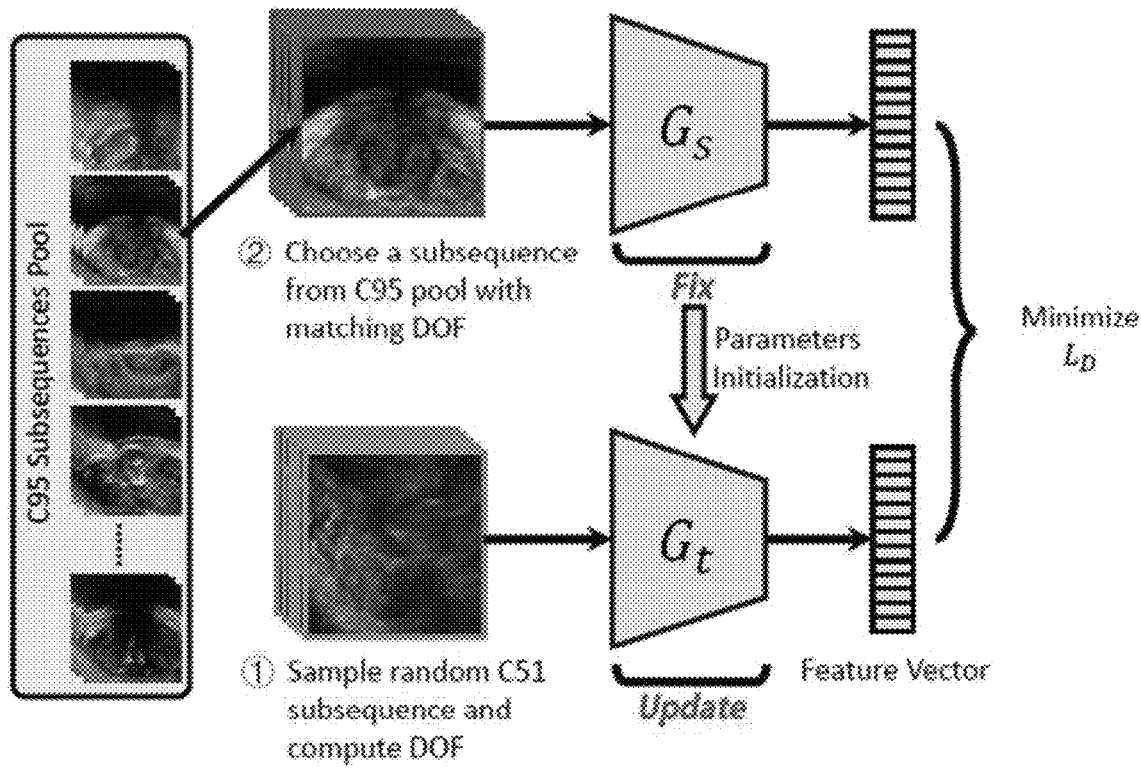
FIG. 9B is a flowchart showing feature vectors discrepancy minimization phase of the exemplary transducer adaptive ultrasound volume reconstruction.
Figure 9C:
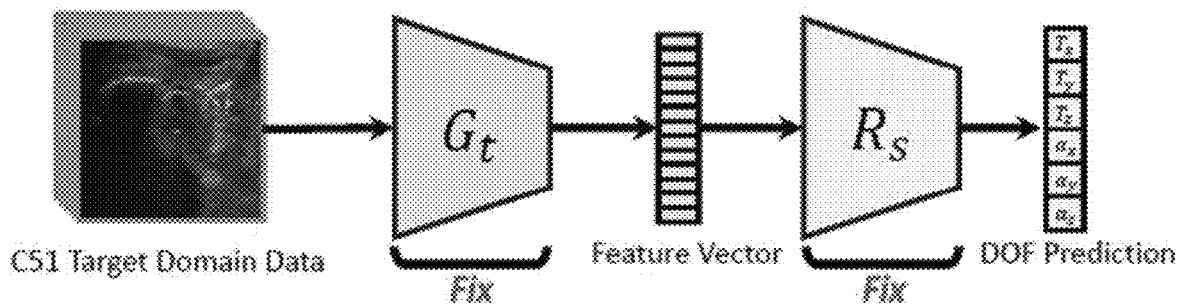
FIG. 9C shows the inference and testing phase of the exemplary transducer adaptive ultrasound volume reconstruction.

In some embodiments, the source domain dataset (e.g., transrectal scans) are denoted as $\{X_s|Y_s\}$, where each image sample $X_s$ represents a subsequence of N=5 consecutive frames and its corresponding label $Y_s$ is a six DOF vector. In some embodiments, the target domain (e.g., transabdominal scans) have a smaller dataset denoted as $\{X_t|Y_t\}$. FIGS. 9A-9C show the method steps of TAUVR according to an exemplary embodiment of the present technology.

As shown in FIG. 9A, a convolutional feature extractor $G_s$ and a DOF regressor $R_s$ are trained in the source domain in an end-to-end fashion. For example, in some embodiments, $G_s$ and $R_s$ are trained as described above regarding system 100 using CNN 20 or DCL-Net 40. The input to $G_s$ is a N×W×H subsequence tensor and the output is a 2048D feature vector. The DOF regressor is a linear layer that outputs six values for DOF regression. $G_s$ and $R_s$ are jointly trained by minimizing the MSE loss between the network's output and the ground-truth DOF labels.

As shown in FIG. 9B, a feature extractor $G_t$ is trained on the target domain which produces domain-invariant features while preserving task-specific information. $G_t$ is initialized with the parameters of $G_s$ and shares the identical structure, and $G_s$'s parameters are preferably fixed in this step. A source domain subsequence pool is created, where every transrectal video subsequence has a corresponding DOF label vector. During adaptation training, for every random target subsequence sample $x_t$, its DOF vector $y_t$ is computed based on labeling information. Next, the pool is searched to find a source domain subsequence $x_s$ that has the closest motion vector as $y_t$. With this paired subsequence serving as the input to corresponding networks, a pair of latent feature vectors is denoted as:

$$v_s = G_s(x_s), v_t = G_t(x_t) \quad (3)$$

$G_t$ is trained by minimizing the discrepancy loss $L_D$, which is the L2 norm between the two generators' output feature vectors:

$$L_D = \frac{1}{P}\sum_{p=1}^{P} \|v_s^p - v_t^p\|_2 \quad (4)$$

where P denotes the total number of samples pairs within one training epoch. This paired sampling strategy establishes correspondence between source and target subsequences because, as the present researchers surprisingly discovered, when two subsequences from different domains have similar motion, their extracted feature vectors are close to each other in the latent space. This paired-sampling strategy takes rich information in the labeled source dataset as a reference to guide task-specific features learning in the target domain. Since the labels of target domain data are only used for sampling subsequence pairs and do not directly contribute to the loss function, this strategy may be categorized as a weakly-supervised method.

As shown in FIG. 9C, TAUVR includes an inference testing phase on the target domain data and preferably does not involve any parameters update. The network used in this step is the concatenation of $G_t$ from FIG. 9B and $R_s$ from FIG. 9A. For a full-length ultrasound video sequence in the target domain test set, a sliding-window procedure is used to get the DOF motion vector prediction for every subsequence. By placing each frame into 3D space accordingly, a 3D ultrasound image volume is reconstructed. This testing phase does not require any tracking devices and the network (e.g., CNN 20 or DCL-Net 40) estimates the ultrasound frames' relative positions.

EXAMPLES

Example 1

According to an exemplary embodiment, a dataset is split into 500, 70, and 70 cases as training, validation, and testing, respectively. The DCL-Net was trained for 300 epochs with batch size K=20 using an Adam optimizer with initial learning rate of $5\times10^{-5}$, which decays by 0.9 after 5 epochs. Since the prostate ultrasound image only takes a relatively small part of each frame, each frame was cropped without exceeding the imaging field and then resized to 224×224 to fit the design of ResNexts. The training phase of the DCL-Net took about 4 hours, taking 5 frames as input. During testing, it took about 2.58 seconds to produce all the transformation matrix of an ultrasound video with 100 frames.

Two evaluation metrics were used for performance evaluation. The first is the final drift, which is the distance between the center points of the transformed end frames of a video segment using the EM tracking data and the DCL-Net estimated motion, respectively. The second is the mean distance between all the corresponding frame corner-points throughout a video. This error reveals the difference in speed and orientation variations across the entire video.

Figure 10:
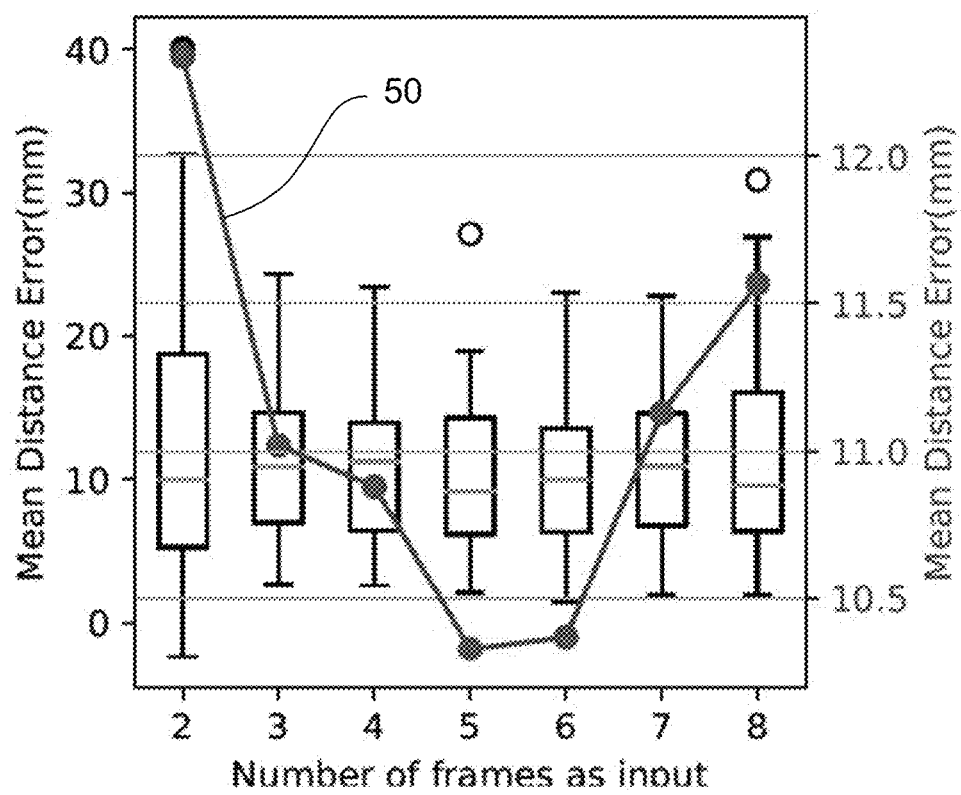
FIG. 10 is a chart comparing the results of an exemplary imaging volume reconstruction method using different number of frames as input.

Experiments were performed to determine an optimal N number of frames for each video segment. FIG. 10 shows how the overall reconstruction performance varies as the number of consecutive frames changes. The green curve plot 50, showing the mean distance error of each experiment, is super imposed onto the boxplot with different y-scales (shown on the right side of the chart) for better illustration. There is a decrease then increase in the error, with neighboring frame number equaling to 5 or 6 has similarly the best performance. According to a paired t-test, the calculated p-value is smaller than the confidence level of 0.05, indicating the result using 5 frames is significantly better than that using only 2 frames. Thus, the network of the present technology takes advantage of the rich contextual information along the time-series and produces more stable trajectory estimation.

Figure 11:
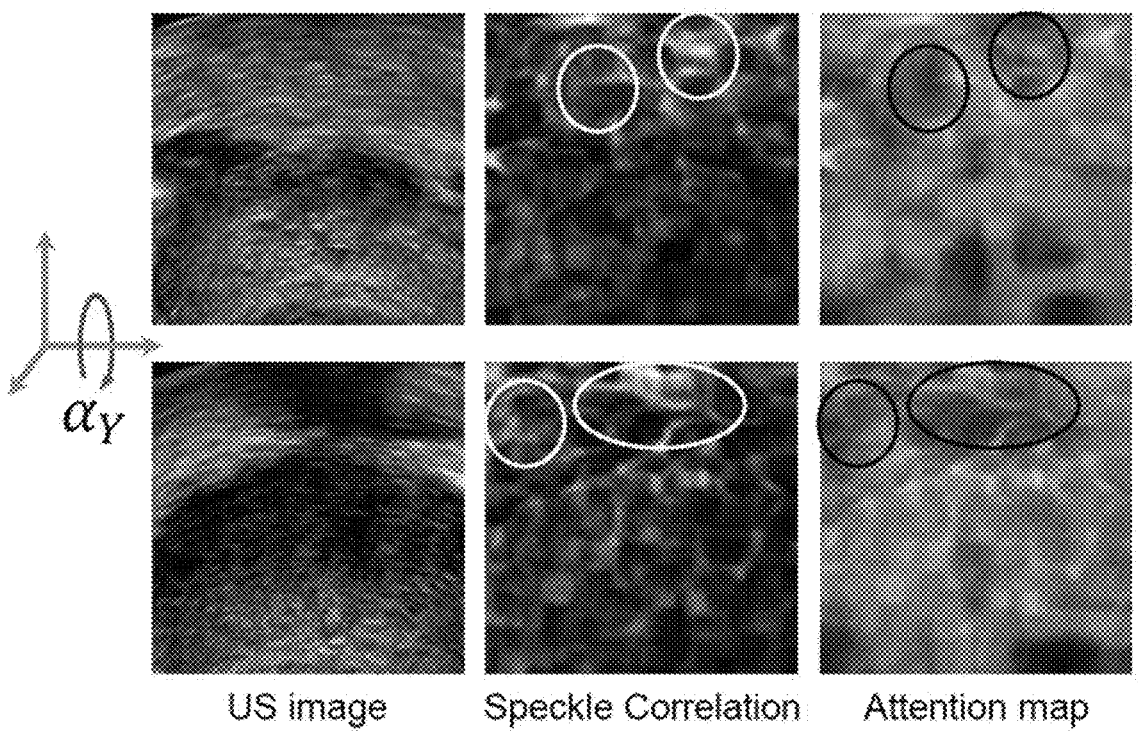
FIG. 11 shows visualizations of attention maps formed by an exemplary imaging volume reconstruction method.

FIG. 11 shows two example attention maps. The left image column shows the cropped ultrasound images. The center column is the speckle correlation map between an ultrasound image and its following neighboring frame. Inside this speckle correlation map, the brighter the area, the longer the elevational distance to the next frame. Such pattern with dark areas at the bottom and brighter on the upper part is consistent with the TRUS scanning protocol used herein, as there is less motion around the tip of the ultrasound probe. The right column shows the attention map regarding the rotation $\alpha_y$ around the Y-axis, which also indicates part of the out-of-plane rotation. The attention maps have strong activation at the bright speckle correlation regions, indicating that the attention module helps the network to focus on speckle-rich areas for better reconstruction.

Table 1, shown below, summarizes the overall comparison of an exemplary embodiment of the DCL-Net of the present technology against prior art methods. The approach of "Linear Motion" means that the mean motion vector of the training set is first calculated and then this fixed vector is applied to all the testing cases. The approach of "Decorrelation" is based on the speckle decorrelation algorithm presented in Chang et al. "2D CNN" refers to the method presented by Prevost et al. "3D CNN" is the basic ResNext architecture taking only two slices as input.

TABLE 1

Performance of different methods on the EM-tracking dataset

| Methods | Distance Error (mm) | | | | Final Drift (mm) | | | |
|---|---|---|---|---|---|---|---|---|
| | Min | Median | Max | Average | Min | Median | Max | Average |
| Linear Motion | 7.17 | 19.73 | 60.79 | 22.53 | 12.53 | 37.15 | 114.02 | 42.62 |
| Decorrelation | 9.62 | 17.58 | 56.72 | 18.89 | 15.32 | 38.45 | 104.13 | 38.26 |
| 2D CNN | 5.66 | 15.80 | 43.35 | 17.42 | 7.05 | 23.13 | 68.87 | 26.81 |
| 3D CNN | 2.38 | 10.14 | 31.34 | 12.34 | 1.42 | 19.08 | 68.61 | 21.74 |
| DCL-Net | 1.97 | 9.15 | 27.03 | 10.33 | 1.09 | 17.40 | 55.50 | 17.39 |

As shown in Table 1, the DCL-Net of the present technology outperforms all the other methods. Paired t-test was performed and the performance improvement made by DCL-Net is significant in all the cases with $p<0.05$.

Figure 12:
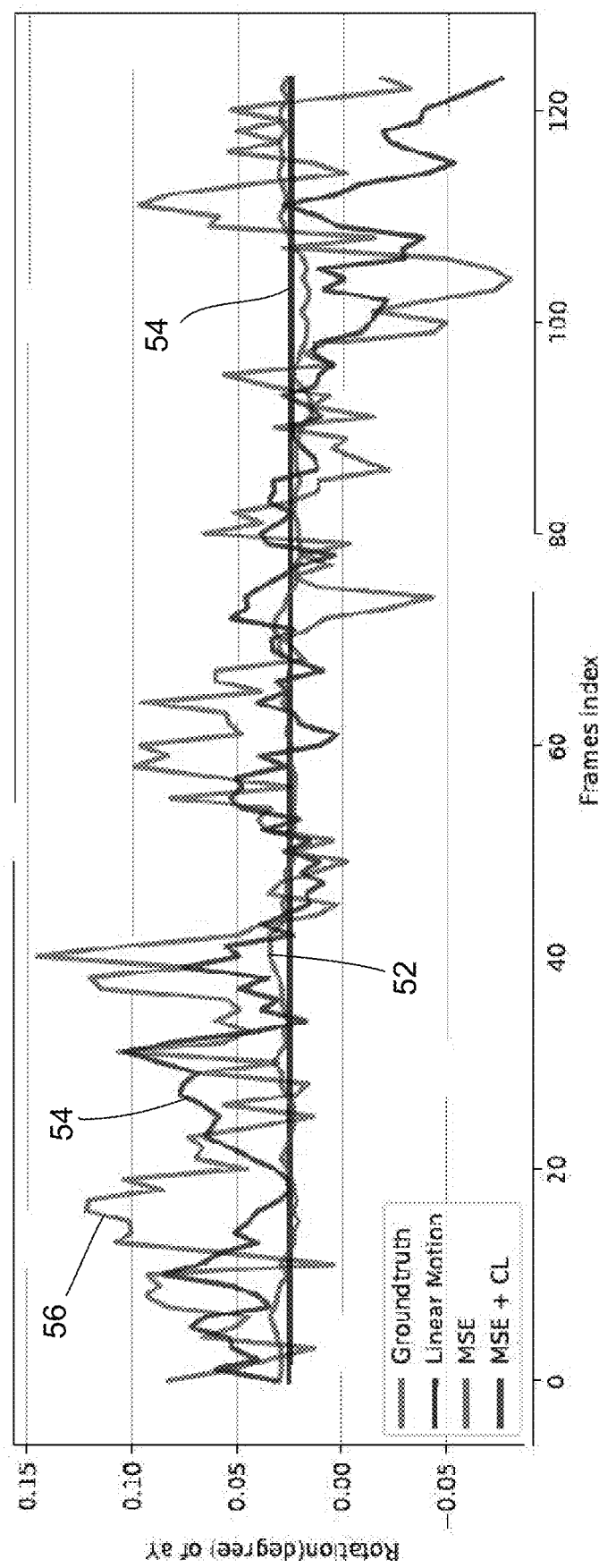
FIG. 12 is a chart showing the predicted rotation along an axis on an ultrasound video sequence by different imaging volume reconstruction methods.
Figure 13A:
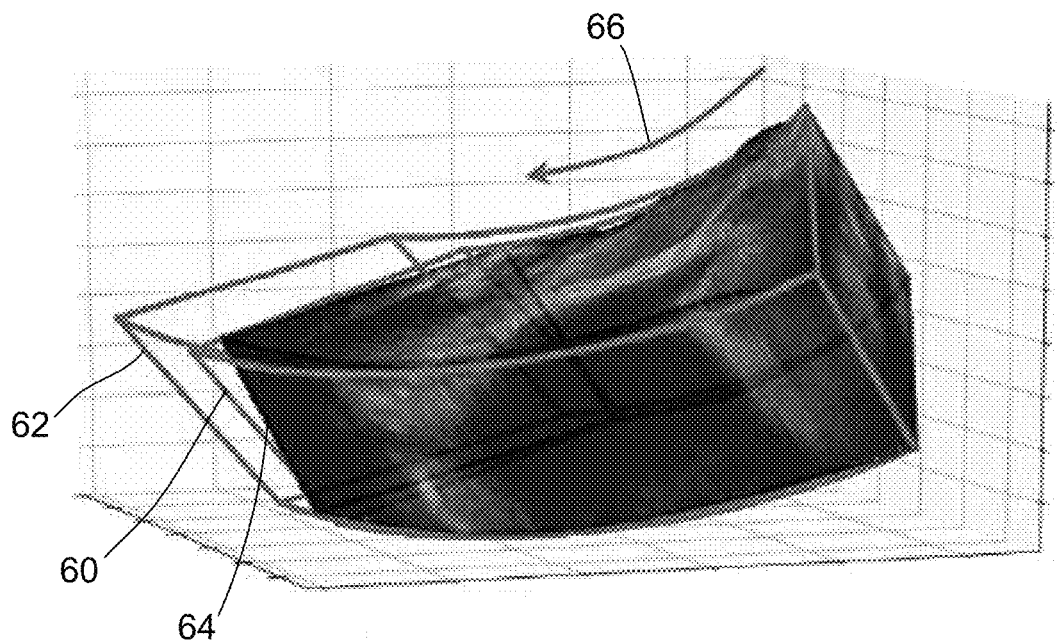
FIGS. 13A-13D are charts comparing the resulting quality of different imaging volume reconstruction methods.
Figure 13B:
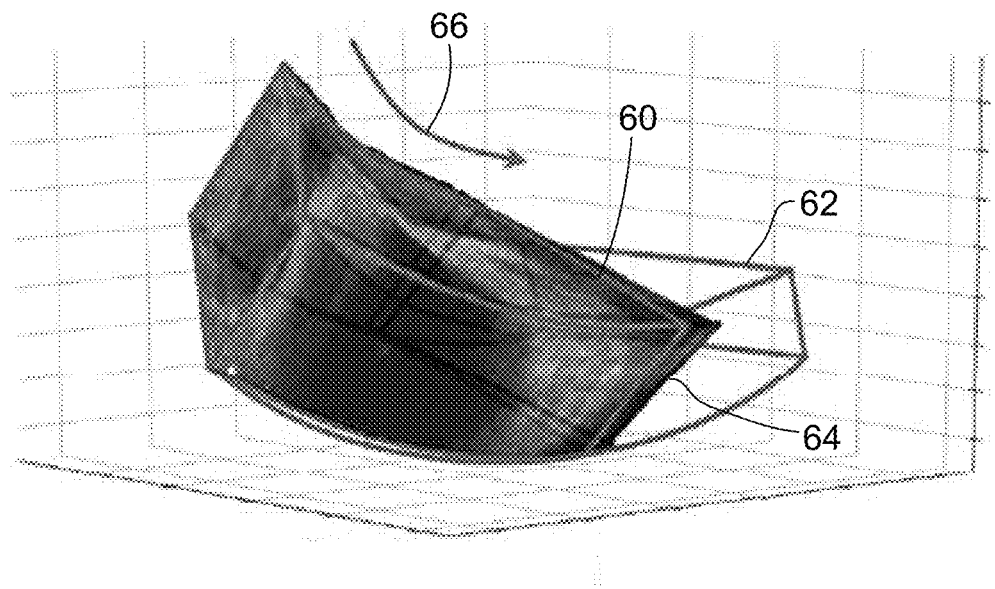
Figure 13C:
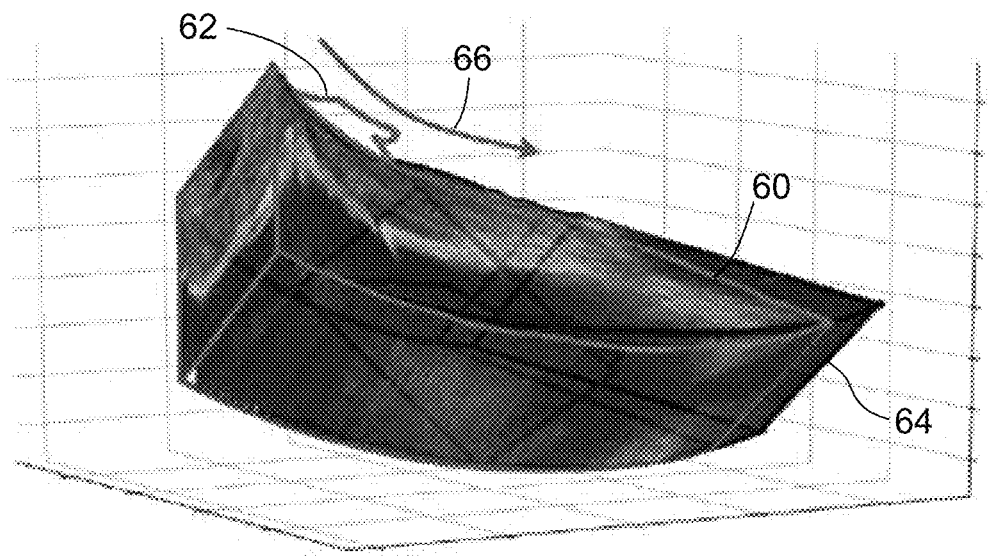
Figure 13D:
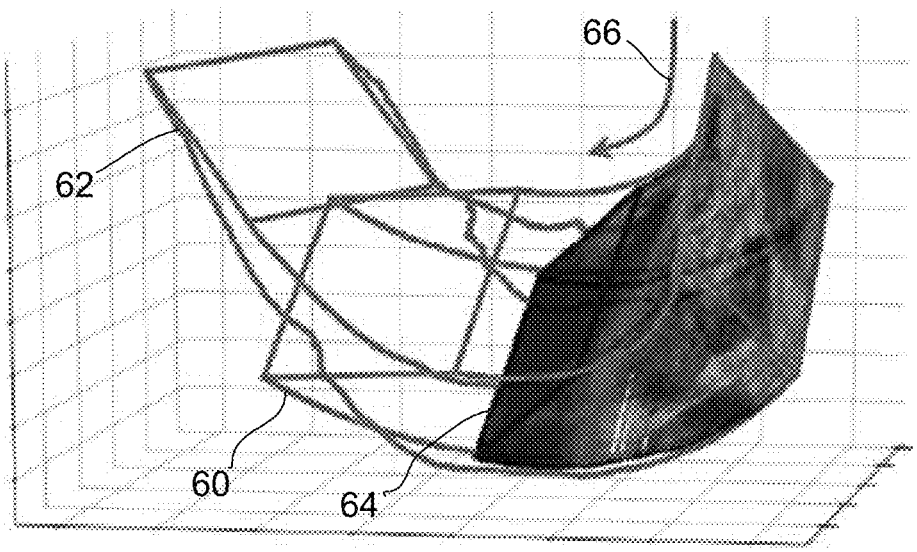

The effectiveness of incorporating case-wise correlation loss was next demonstrated. FIG. 12 shows the prediction of $\alpha_y$ along a video sequence. As shown, the network trained only with MSE loss produces mediocre results (red line 52), which is nearly constant, showing almost no sensitivity to the change in speed and orientation. By incorporating the correlation loss ("CL") into the loss function (blue line 54), the prediction of the network reacts more sensitively to the variation of the probe's translation and rotation. The ground-truth (green line 56) and linear motion (black line 58) results are also plotted.

FIGS. 13A-13D show the volume reconstruction results using four testing cases with different reconstruction qualities. One good case (FIG. 13A), one bad case (FIG. 13D), and two median cases (FIGS. 13B-13C) are shown to offer a complete view of the performance. To reduce the clutter in the figures, only the comparison between the DCL-Net (green line 60) of the present technology, the 2D-CNN (blue line 62), and the ground-truth (black line 64) are shown. The probe trajectory is shown by the red curved arrow 66. While producing competitive performance, the 2D-CNN method is less sensitive to the speed variations of ultrasound probe and the estimated trajectory has noisy vibration. The results sometimes even severely deviate from the ground-truth. The DCL-Net of the present technology shows a much smoother trajectory estimation due to the contextual information provided by video segments.

Example 2

According to another exemplary embodiment, TAUVR was tested. The source domain contained 640 transrectal ultrasound video sequences, with each frame corresponding to a positioning matrix captured by an EM-tracking device. An end-firing C95 transrectal ultrasound transducer captured axial images by steadily sweeping through the prostate from base to apex. The dataset was split into 500, 700, and 70 cases as training, validation, and testing. The target domain contained 12 transabdominal ultrasound video sequences acquired by a C51 ultrasound transducer. Nine cases were used for the training described above with reference to FIG. 9B and the network's parameters were saved after every epoch. Three cases were used for the testing described above with reference to FIG. 9C.

Four baseline methods are presented for comparison. As shown in FIG. 14, "Source" was trained on source domain and then directly tested on target domain, "Target" works in the opposite way, "Mixed" is trained on merged source and target domain using all available label for supervision, and "ADDA" uses unsupervised adversarial domain adaptation method to extract domain-invariant features. TAUVR achieved significantly lower average distance error and final drift comparing to both "Source" and "ADDA." TAUVR is also comparable to the results of "Target," while the latter still has a huge domain shift problem between source and target domain because of the model's over-fitting to the transabdominal dataset.

Figure 15:
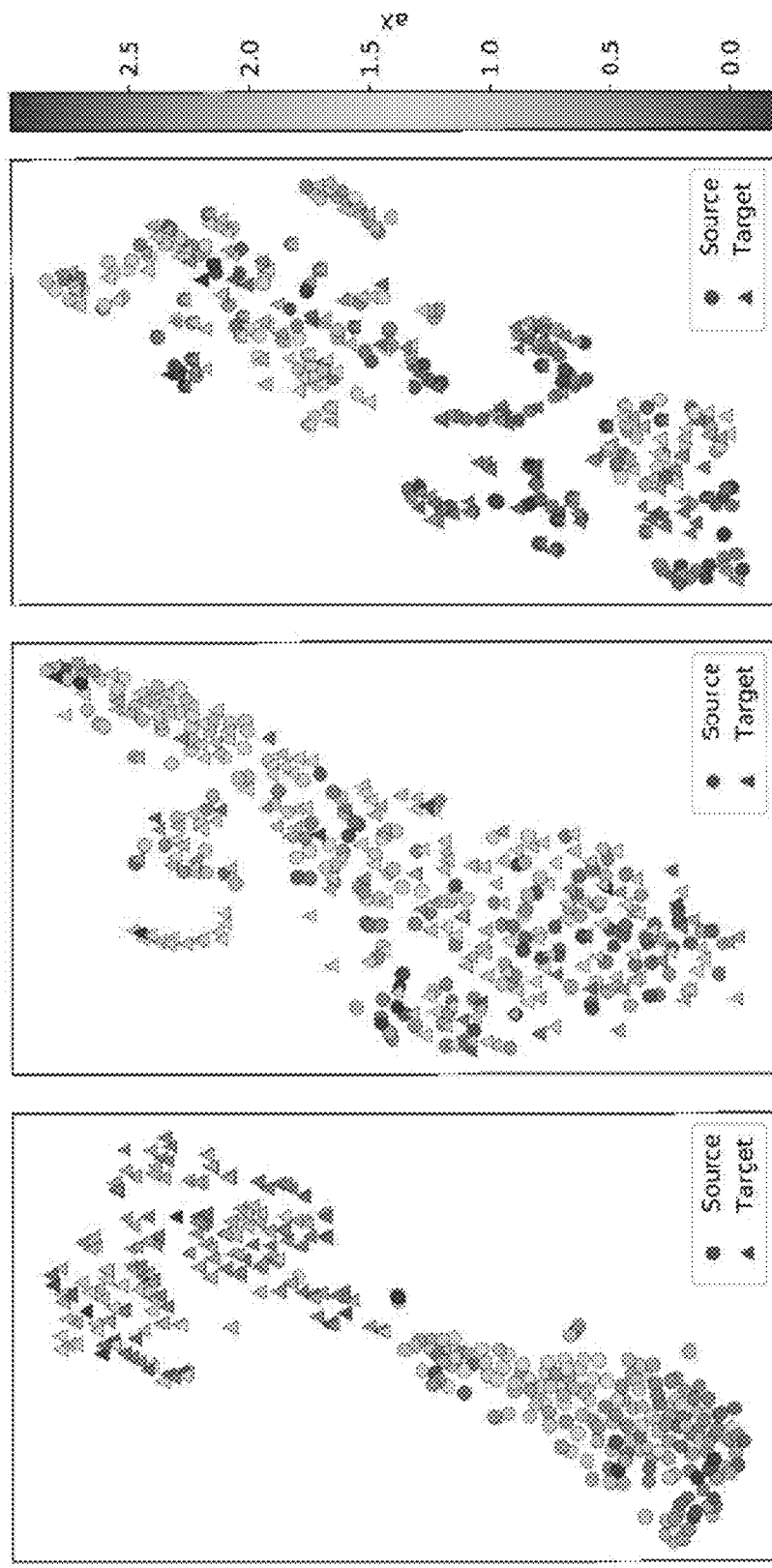
FIG. 15 is a chart comparing 2D projections of the latent feature vectors of two different ultrasound scan video sequences obtained using different imaging volume reconstruction methods.

The quality of the features were evaluated through latent vector projections. As shown in FIG. 15, 2D t-SNE projections of the extracted 2048D feature vectors were plotted, using the most dominant motion aX for color encoding. In the left chart, points from the source domain and the target domain were roughly separated into two clusters, and within each cluster there existed a continuous changing pattern in aX encoding. This indicates that (1) the network trained on source domain exhibits a domain gap on target data, and (2) the network, however, still preserves the task-specific information in feature vectors. The center chart shows that the distributions of two domains have been merged together through ADDA. However, since unsupervised learning poses no constraint on task-specific feature learning, the smooth colo transition pattern disappears in the target domain (triangles), resulting in uninformative feature learning. The right chart shows that TAUVR successfully merges the distributions of two domains and keeps a gradual color transition in aX for each domain. Thus, benefited by the pair-sampling strategy discussed above, TAUVR extracts domain-invariant features while still preserving task-specific feature learning in both domains.

Figure 16:
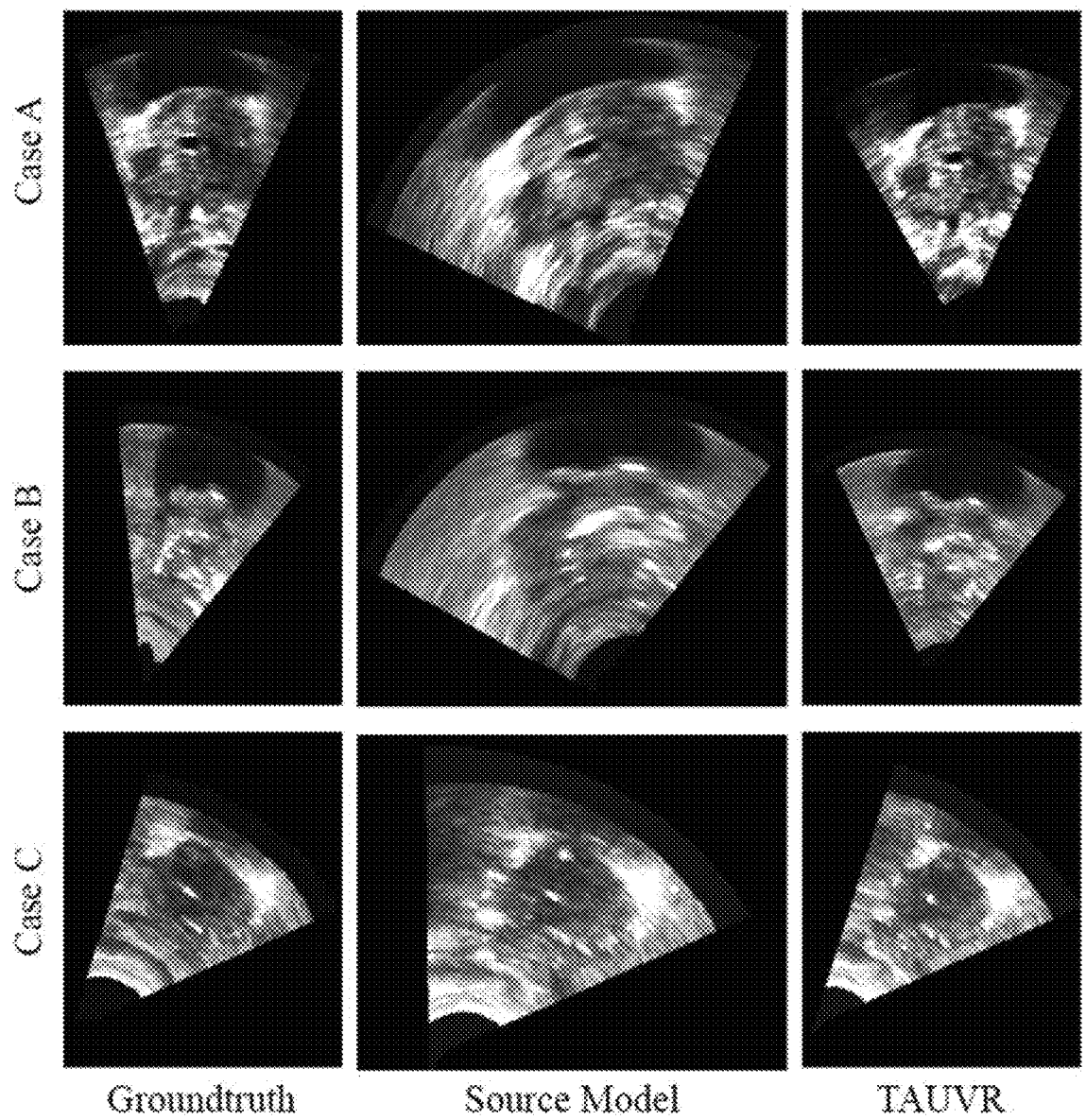
FIG. 16 shows ultrasound images comparing the reconstructed ultrasound volumes obtained using different imaging volume reconstruction methods.

FIG. 16 shows sagittal views of the reconstructed volumes for quality assessment. All three test cases in the target domain (transabdominal scans) are presented by rows. From left to right, each column represents the reconstruction results from ground-truth labels, model trained only on source domain, and TAUVR. As shown in the figure, by directly applying source model to the target data, the deep neural network may exhibit an over-fitting pattern that produces transducer trajectory prediction very close to that of the source domain. In other words, the trajectory prediction is deviated from the actual trajectory in the transabdominal scans. By incorporating the pairwise domain adaptation method discussed above, the right column (TAUVR) produces visually much closer volume reconstruction comparing with the ground-truth.

Accordingly, embodiments of the present technology are directed to a sensorless freehand 3D ultrasound volume reconstruction method based on deep learning. The DCL-Net of the present technology extracts the information among multiple ultrasound frames to improve the ultrasound probe trajectory estimation. Experiments on a well-sized EM-tracked ultrasound dataset demonstrated that the DCL-Net has benefited from the contextual learning and showed superior performance when compared to other existing methods. Embodiments are also directed to a pair-sampling strategy to enhance task-specific feature learning in target domain, using matched source domain samples as reference. TAUVR allows sensorless ultrasound volume reconstruction, yielding a network that is capable of extracting domain-invariant features and preserve task-specific feature learning. TAUVR achieves promising results on target domain while the performance does not degrade on source domain.

Although the technology has been described and illustrated with respect to exemplary embodiments thereof, it should be understood by those skilled in the art that the foregoing and various other changes, omissions, and additions may be made therein and thereto, without parting from the spirit and scope of the present technology.

What is claimed is:

1. A method of ultrasound image volume reconstruction, the method comprising:
   receiving a first dataset comprising at least one pair of consecutive ultrasound images;
   inputting the first dataset to a convolutional neural network ("CNN");
   training the CNN with the first dataset;
   receiving a second dataset comprising an ultrasound video comprising a plurality of consecutive ultrasound images;
   inputting the second dataset to the CNN; and
   processing, by the CNN, the second dataset to produce as output a reconstructed 3D ultrasound image volume;
   wherein the CNN comprises a spatial transformation network ("STN") and a loss function; and
   wherein the loss function comprises:
     a mean squared error loss between the outputs of a localization network of the STN and a ground-truth six degrees of freedom of the first dataset; and
     an image similarity loss between a reconstructed 3D ultrasound image volume of the STN and the ground-truth.

2. The method of claim 1, wherein the STN comprises a localization network, a grid generator, and an image sampler.

3. The method of claim 2 wherein the localization network is configured to produce a plurality of transformation parameters for determining a position of a second image of the at least one pair of consecutive ultrasound images relative to a first image of the at least one pair of consecutive ultrasound images.

4. The method of claim 3, wherein the grid generator is configured to receive the plurality of transformation parameters as input and generate a plurality of 3D grids as output.

5. The method of claim 4, wherein the image sampler is configured to produce a reconstructed 3D ultrasound image volume by locating corresponding pixel values in the first image and the second image and filling in the plurality of 3D grids with the corresponding pixel values.

6. The method of claim 1, wherein the ultrasound video of the second dataset is obtained from a trackingless ultrasound scan such that the second dataset does not include positional information.

7. The method of claim 1, wherein the first dataset is obtained by a first ultrasound transducer and the second dataset is obtained by a second ultrasound transducer, the first ultrasound transducer and the second ultrasound transducer are configured to perform different ultrasound scans.

8. The method of claim 7, wherein the first ultrasound transducer is configured to perform transrectal ultrasound scans and the second ultrasound transducer is configured to perform transabdominal ultrasound scans.

9. The method of claim 7, wherein processing the second dataset comprises:
   aligning a first image of the ultrasound images of the first dataset and a first image of the ultrasound images of the second dataset;
   computing a degree of freedom motion vector for each ultrasound image of the first dataset and the second dataset;
   forming a subsequence pool for the first dataset based on the degree of freedom motion vectors for the ultrasound images of the first dataset;
   searching, for each degree of freedom motion vector of the ultrasound images of the second dataset, the subsequence pool for a degree of freedom motion vector of the ultrasound images of the first dataset that most closely matches the motion vector of the ultrasound image of the second dataset; and
   forming a paired subsequence for each matching motion vectors of the first dataset and the second dataset.

10. A method of ultrasound image volume reconstruction, the method comprising:
    receiving a first dataset comprising at least one pair of consecutive ultrasound images;
    inputting the first dataset to a convolutional neural network ("CNN");
    training the CNN with the first dataset;
    receiving a second dataset comprising an ultrasound video comprising a plurality of consecutive ultrasound images;
    inputting the second dataset to the CNN; and
    processing, by the CNN, the second dataset to produce as output a reconstructed 3D ultrasound image volume;
    wherein the first dataset is obtained by a first ultrasound transducer and the second dataset is obtained by a second ultrasound transducer, the first ultrasound transducer and the second ultrasound transducer are configured to perform different ultrasound scans; and
    wherein processing the second dataset comprises:
    aligning a first image of the ultrasound images of the first dataset and a first image of the ultrasound images of the second dataset;
    computing a degree of freedom motion vector for each ultrasound image of the first dataset and the second dataset;
    forming a subsequence pool for the first dataset based on the degree of freedom motion vectors for the ultrasound images of the first dataset;
    searching, for each degree of freedom motion vector of the ultrasound images of the second dataset, the subsequence pool for a degree of freedom motion vector of the ultrasound images of the first dataset that most closely matches the motion vector of the ultrasound image of the second dataset; and
    forming a paired subsequence for each matching motion vectors of the first dataset and the second dataset.

11. The method of claim 10, wherein the CNN comprises a spatial transformation network ("STN") and a loss function.

12. The method of claim 11, wherein the STN comprises a localization network, a grid generator, and an image sampler.

13. The method of claim 12, wherein the localization network is configured to produce a plurality of transformation parameters for determining a position of a second image of the at least one pair of consecutive ultrasound images relative to a first image of the at least one pair of consecutive ultrasound images.

14. The method of claim 13, wherein the grid generator is configured to receive the plurality of transformation parameters as input and generate a plurality of 3D grids as output.

15. The method of claim 14, wherein the image sampler is configured to produce a reconstructed 3D ultrasound image volume by locating corresponding pixel values in the first image and the second image and filling in the plurality of 3D grids with the corresponding pixel values.

16. The method of claim 11, wherein the loss function comprises:
   a mean squared error loss between the outputs of a localization network of the STN and a ground-truth six degrees of freedom of the first dataset; and
   an image similarity loss between a reconstructed 3D ultrasound image volume of the STN and the ground-truth.

17. The method of claim 10, wherein the ultrasound video of the second dataset is obtained from a trackingless ultrasound scan such that the second dataset does not include positional information.

* * * * *